United States Patent [19]

Gallot et al.

[11] Patent Number: 4,600,526

[45] Date of Patent: Jul. 15, 1986

[54] LIPOPEPTIDES, THEIR PREPARATION AND THEIR APPLICATION AS EMULSIFIERS

[75] Inventors: Bernard Gallot; André Douy, both of Olivet, France

[73] Assignee: Centre National de la Recherche Schientifique (C N R S), Paris, France

[21] Appl. No.: 533,428

[22] Filed: Sep. 16, 1983

[30] Foreign Application Priority Data

Sep. 22, 1982 [FR] France .............................. 82 15976

[51] Int. Cl.⁴ ..................... C09K 19/52; B01J 13/00
[52] U.S. Cl. ......................... 252/299.01; 252/315.1; 424/78; 514/2; 514/938; 530/324; 530/359
[58] Field of Search .................. 252/299.01, 315.1; 260/112.5 R, 112 R

[56] References Cited

U.S. PATENT DOCUMENTS

| | | | |
|---|---|---|---|
| 2,958,665 | 11/1960 | Stefcik et al. .................. | 252/315.1 |
| 3,064,047 | 11/1962 | Miller .......................... | 252/315.1 X |
| 4,299,821 | 11/1981 | Kisfaludy et al. .............. | 260/112.5 R |
| 4,301,045 | 11/1981 | Kaiser et al. .................. | 260/112.5 R |
| 4,308,181 | 12/1981 | McGregor ...................... | 260/112.5 R |
| 4,310,517 | 1/1982 | Etschenberg et al. ... | 260/112.5 R X |

FOREIGN PATENT DOCUMENTS

52-66885  6/1977  Japan ................................ 252/315.1

OTHER PUBLICATIONS

Tsutsui, et al., *Mol. Cryst. Liq. Cryst.*, vol. 56 (Letters) pp. 57-61, 1979, "Topological Polymer . . . ".

Kubo, *Mol. Cryst. Liq. Cryst.*, vol. 74, pp. 71-87, 1981, "Thermodynamic Properties of Poly(benzyl-glutamate) . . . ".

Laupretre, *Journal de Physique*, 7 Congres International sur les Cristaux Liquides, Bordeaux, France, 1978, pp. C3-478-480, "Relations Entre le Caractere Mesogene . . . ".

Kakinuma, et al., *Experientia*, v. 24(11) pp. 1120-1121, 1968, "Peptidelipid Surfactant".

Brown, et al., Liquid Crystals & Biological Structures, Academic Press, 1979, excerpts, pp. 36-37, 40, 56-57, 71.

Vogl, et al., *Polymer Preprints*, vol. 19, No. 2, Sep. 1978, "Functional Condensation . . . ", pp. 75-80.

Douy, et al, *Polymer Preprints*, vol. 18, No. 2, Aug. 1977, "Mesomorphic Order . . . ", pp. 51-55.

Moroder, et al., Hoppe-Seyler's, *Z. Physiol. Chem.*, Bd. 357, S. 1651-53, Nov. 1976, "Di-tert-butyl-dicarbonate . . . ".

Werner, *Chem. Abstr.*, vol. 97, No. 23, 192611x, Dec. 6, 1982.

Garg, *Chem. Abstr.*, vol. 73, No. 23, 116276f, Dec. 7, 1970.

Czarniecka, "Polypeptide Liquid Crystals: A Deuterium NMR Study", *Mol. Cryst. Liq. Cryst.*, vol. 63, pp. 205-214, 1981.

*Primary Examiner*—Teddy S. Gron
*Assistant Examiner*—Catherine S. Kilby
*Attorney, Agent, or Firm*—Berman, Aisenberg & Platt

[57] ABSTRACT

The lipopeptides according to the invention are amphiphatic and consist of a hydrophobic chain containing from about 8 to 24 carbon atoms and of a peptide chain which is hydrophilic or has been rendered hydrophilic.

They are applied, in particular, to emulsions of immiscible media and to the preparation of lyotropic liquid crystals.

15 Claims, 4 Drawing Figures

LIPOPEPTIDES, THEIR PREPARATION AND THEIR APPLICATION AS EMULSIFIERS

FIELD OF THE INVENTION

The present invention relates to the synthesis of lipopetides, and more particularly of amphiphatic lipopeptides, and to the application of these compounds as emulsifiers or as liquid crystals.

SUMMARY OF THE INVENTION

The invention relates firstly to a new class of lipopeptides which are amphiphatic lipopeptides composed of a hydrophobic chain containing at least about 8 carbon atoms and preferably from about 8 to 24 carbon atoms, and of a peptide chain which is hydrophilic or has been rendered hydrophilic.

The lipopeptides according to the invention can be defined by the general formula:

$$CnPP$$

in which Cn represents a hydrophobic chain having at least about 8 carbon atoms and preferably about 8 to 24 carbon atoms, n denoting the number of carbon atoms, and PP represents a polypeptide obtained from natural aminoacids or their derivatives (having the l or d configuration). In practice, the polypeptide PP is formed of one or more aminoacids, depending on the chosen degree of polymerization, which can be 1 or more. The nomenclature of some of the most common peptide sequences which can be used is summarized later in Table I.

The term "hydrophobic chain" is understood as meaning preferably, but not exclusively, an optionally substituted, aliphatic hydrocarbon chain having the indicated number of carbon atoms.

These compounds have been obtained by a technique which is itself novel.

The invention therefore also relates to a process for the preparation of amphiphatic lipopeptides as defined above, which basically consists in:

(1) producing a peptide linkage between a fatty amine and an N-protected aminoacid to give a lipopeptide whose peptide chain has a degree of polymerization of 1, and, if it is desired to obtain a degree of polymerization of 2 or 3 for the peptide chain, producing a further peptide linkage between an N-protected aminoacid and the product whose degree of polymerization is 1 lower, or (2a) carrying out the polymerization of the N-carboxyanhydride of the aminoacid by initiating it with the fatty amine $CnNH_2$ to give lipopeptides whose peptide chains have a degree of polymerization which will depend on the operating conditions chosen, and (2b) if desired, fractionating the lipopeptides from step (2a) in respect of their composition, and (3) except in the case where the peptide chain of the product from step (1) and/or (2a) or (2b) is directly a hydrophilic chain, unblocking the side chains of the hydrophobic peptide chain in order to render them hydrophilic.

To obtain lipopeptides having a degree of polymerization of 1, 2 or 3, a possible procedure is to produce a peptide linkage between the fatty amine of the formula $CnNH_2$, where Cn is as defined above, and the aminoacid whose amino nitrogen atom is protected, for example by the tert.-butoxycarbonyl group (abbreviated to Boc), and this amino nitrogen atom is unblocked to give the product having a degree of polymerization of 1, which will be coupled again with the blocked aminoacid to give the product having a degree of polymerization of 2, after unblocking of the terminal nitrogen, and so on.

To obtain the lipopeptides according to the invention, it is also possible to polymerize the N-carboxyanhydride (abbreviated to NCA) of the aminoacid, the polymerization being initiated by the fatty amine $CnNH_2$. If desired, fractionation in respect of composition is then carried out (the lipid sequence being monodisperse) by selective precipitation of the lipopeptides, and a series of lipopeptides are obtained which differ in their peptide composition.

The monomeric peptides used are commercial products or are prepared in a known manner.

The monomer used for the peptide part of the lipopeptides according to the invention is not therefore the aminoacid itself but its cyclic derivative, namely the aminoacid N-carboxyanhydride (NCA), obtained by reacting phosgene with the aminoacid, according to the equation:

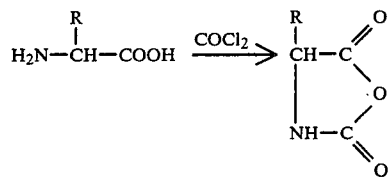

or with the aminoacid N-protected by one of the groups normally used in peptide synthesis.

The NCA compounds are prepared in THF by reacting a solution of phosgene in tetrahydrofuran (THF) with the aminoacid. This method is a modified version of the method of Fuller, Verlander and Goodman (Biopolymers, 15, 1869/1976), in which the solvent for the phosgene is benzene.

The fatty amine $CnNH_2$ is a commercially available amine, or an amine obtained from the fatty acid having one carbon atom more by means of Schmidt's degradation reaction using sodium azide in a strong acid medium [Indian J. Technol., 5, 262 (1967)], or an amine obtained by coupling acryloyl or methacryloyl chloride with a primary diamine, or an N-protected aminoalcohol. The choice of a chain Cn having from about 8 to 24 carbon atoms is not critical but results solely from the greater availability of the corresponding products. This hydrophobic chain Cn can be any hydrocarbon chain, but it can also contain substituents and/or heteroatoms provided that they do not have an unfavorable influence on the synthesis process.

The preparation of hydrophobic lipopeptides and their conversion to amphiphatic lipopeptides, and the direct preparation of amphiphatic lipopeptides, are described successively below, with reference to the nomenclature given in Table I.

BRIEF DESCRIPTION OF THE DRAWINGS

The infrared spectra (in KBr) of certain derivatives of the invention herein are shown in FIGS. 1–4; C18 Sar$_{11}$, and C16 Sar$_{1,2,3}$ respectively.

A-1 Synthesis of Hydrophobic Lipopeptides ($CnEb_p$, $CnDb_p$ and $CnKt_p$)

Figure 1:
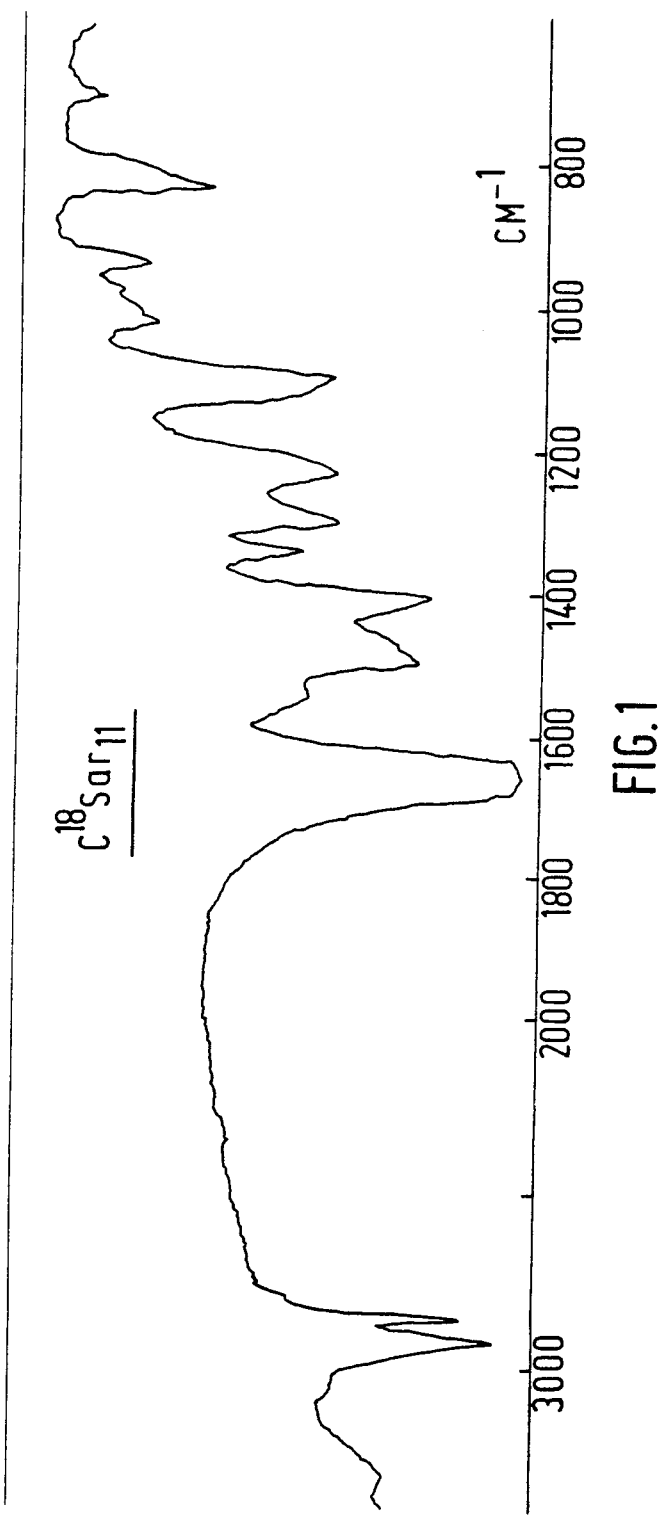

The fatty amine ($CnNH_2$) is dissolved in chloroform, the NCA of the appropriate aminoacid is then added and the mixture is left to polymerize at ambient temperature for two days, with agitation. This gives the lipopeptides $CnEb_p$ possessing a peptide sequence of poly(benzyl glutamate), $CnDb_p$ possessing a peptide sequence of poly(benzyl aspartate) and $CnKt_p$ possessing a peptide sequence of polytrifluoroacetyllysine.

By way of example, lipopeptides $C17Kt_p$ are synthesized using heptadecylamine, $C_{17}H_{35}NH_2$, obtained from stearic acid (see Indian J. Technol., 5, 262 (1967)). More precisely, to obtain $C17Kt_{10}$, having a degree of polymerization of 10 (DP=10), 27 g (0.1 mole) of trifluoroacetyllysine NCA are added to a solution of 2.55 g (0.01 mole) of C17 amine in 150 ml of chloroform, and the mixture is left to polymerize at ambient temperature for several hours, with agitation. The chloroform is then evaporated off, the residue is taken up in methanol and the polymer is precipitated in water and then filtered off, washed and dried.

A-2 Conversion of Hydrophobic Lipopeptides to Amphiphatic Lipopeptides

1. Lipopeptides $CnK_p$

The lipopeptides $CnK_p$ possessing a hydrophilic sequence of polylysine (K) were prepared from the lipopeptides $CnKt_p$ by the method of Sela et al. [Biopolymers, 1, 517 (1963)]. A solution of the lipopeptides $CnKt_p$ in THF is treated firstly with a solution of piperidine in methanol and then with a solution of piperidine in water.

As an example illustrating a conversion of $C17Kt_p$ to $C17K_p$, 5 g of $C17Kt_p$ are dissolved in 150 ml of a molar solution of piperidine in methanol at ambient temperature. After 2 hours, 100 ml of a molar solution of piperidine in water are added and the mixture is left for 48 hours at ambient temperature. The methanol is removed in an evaporator and the aqueous solution is passed through a column of anion exchange resin (Duolite A 102D, $OH^-$ form) in order to remove the trifluoroacetate anions therefrom, and the eluate is lyophilized to recover the $C17K_p$.

2. Lipopeptides $CnE_p$ and $CnD_p$

The lipopeptides $CnE_p$ possessing a hydrophilic sequence of polyglutamic acid (E) and $CnD_p$ possessing a hydrophilic sequence of polyaspartic acid (D) are obtained from the lipopeptides $CnEb_p$ and $CnDb_p$ by treating these lipopeptides with HCl and HBr at ambient temperature [J. Am. Chem. Soc., 80, 4631 (1958)].

3. Lipopeptides $CnEp_p$

The lipopeptides $CnEp_p$ possessing a hydrophilic sequence of polyhydroxypropylglutamine (Ep) are prepared by treating the lipopeptides $CnEb_p$ with aminopropanol at 60° C., in solution in dioxane [Biopolymers, 3, 625 (1965)].

4. Lipopeptides $CnEe_p$

The lipopeptides $CnEe_p$ possessing a hydrophilic sequence of polyhydroxyethylglutamine (Ee) are prepared by treating the lipopeptides $CnEb_p$ with ethanolamine at 60° C., in solution in dioxane [Biopolymers, 9, 717 (1970)].

B Direct Synthesis of Amphiphatic Lipopeptides

The fatty amine $CnNH_2$ is dissolved in chloroform, the aminoacid NCA is then added and the mixture is left to polymerize at ambient temperature for 2 days, with agitation. This gives the lipopeptides $CnSar_p$ possessing a peptide sequence of polysarcosine.

In order to give a more concrete illustration of the process for the synthesis of lipopeptides according to the invention, the synthesis of the amphiphatic lipopeptides $C17Sar_p$, formed of an aliphatic chain containing 17 carbon atoms (C17) and of a polysarcosine chain $(Sar)_p$, and the synthesis of $C12Sar_{20}$ and $C18Sar_{11}$, are described below.

1. Synthesis of lipopeptides having a degree of polymerization of more than 3

(a) Synthesis of $C17Sar_{20}$

Heptadecylamine ($C17NH_2$), obtained from stearic acid [see Indian J. Technol., 5, 262 (1967)], is first dissolved in chloroform, and the amount of sarcosine NCA calculated to give the chosen degree of polymerization is then added to the solution. For example, if it is desired to obtain $C17Sar_{10}$, having a degree of polymerization of 10 (DP: 10), 11.5 g of sarcosine NCA (0.1 mole) are added to a solution of 2.55 g (0.01 mole) of amine, $C_{17}H_{35}NH_2$, in 100 ml of chloroform, and the mixture is left to polymerize at ambient temperature for 48 hours, with agitation.

The lipopeptides $C17Sar_p$ are fractionated by fractional precipitation using dimethylformamide as the solvent and acetone as the precipitating agent.

(b) Synthesis of $C12Sar_{20}$ 23 g (0.2 mole) of sarcosine NCA are added to a solution of 1.85 g (0.01 mole) of dodecylamine in 100 ml of chloroform, and the mixture is left to polymerize at ambient temperature for 48 hours, with agitation. The lipopeptides $C12Sar_p$ can be fractionated by fractional precipitation using the precipitating solvents dimethylformamide/acetone.

This gives xg of the desired white solid product, the degree of polymerization of which was measured by determining the terminal amine group after the degree of purity had been checked by chromatography.

(c) Synthesis of $C18Sar_{11}$ $C18Sar_{11}$ is prepared by applying the same operating conditions as under (b), with 0.11 mole of sarcosine NCA (12.65 g) and 0.01 mole of $C18NH_2$ (2.69 g) in 100 ml of chloroform, and is obtained with a yield of more than 80%; its infrared spectrum in KBr is the subject of FIG. 1.

2. Synthesis of lipopeptides having degrees of polymerization of 1, 2 and 3

To obtain lipopeptides having degrees of polymerization of 1, 2 and 3, a possible procedure is to produce a peptide linkage between the fatty amine and the aminoacid N-protected by the tert.-butyloxycarbonyl (Boc) group.

The Boc-aminoacids are prepared from the aminoacid and di-tert.-butyl dicarbonate by the method of Morsder et al. [Hoppe-Seyler's Z. Physiol. Chem., 357, 1651 (1976)].

(a) Synthesis of $C17Sar_1$ ($\alpha$) $C17BocSar_1$: the product $C17BocSar_1$ is obtained by coupling heptadecylamine with $BocSar_1$ in the presence of dicyclohexylcarbodiimide (DCCI). 3.78 g (0.02 mole) of BocSar and 2.06 g (0.01 mole) of DCCI are mixed cold (at 0° C.) in 100 ml of chloroform. A copious precipitate of dicyclohexylurea (DCU) is formed. The mixture is left for 30 minutes at 0° C., with agitation, and 2.55 g (0.01 mole) of heptadecylamine are added. The reaction is left to proceed for 20 hours. The precipitate is filtered off and washed, the filtrate is recovered, the chloroform is evaporated off, the residue is taken up in 50 ml of THF, the mixture is cooled to 0° C. and filtered to remove the maximum amount of dicyclohexylurea, and the precipitate is washed with the minimum amount of cold THF.

($\beta$) C17Sar$_1$.HCl: 20 ml of a 5N solution of HCl in THF are added to the filtrate, and the mixture is left for 24 hours at ambient temperature, with agitation. A copious precipitate of C17Sar$_1$.HCl is formed, which is filtered off and washed with THF.

($\gamma$) C17Sar$_1$: the precipitate is taken up in 100 ml of THF, the mixture is heated to 50° C., 2 ml of triethylamine are then added and the mixture is left to stand for 2 hours. It is cooled to 0° C., the precipitate of triethylamine hydrochloride is filtered off, the THF is evaporated off and the C17Sar$_1$ is recrystallized from acetone.

This gives 2.1 g of C17Sar$_1$ (yield: 65%).

Melting point=58° C.

(b) Synthesis of C17Sar$_3$

To obtain C17Sar$_3$, the same procedure is followed except that C17Sar$_2$ and BocSar are used as the starting materials.

Melting point=83° C.

(c) Synthesis of C17Sar$_2$

To obtain C17Sar$_2$, the procedure is the same except that C17Sar$_1$ and BocSar are used as the starting materials.

Melting point=74° C.

(d) Synthesis of C12Sar$_1$

Preparation of C12SarBoc: 1.85 g (0.01 mole) of dodecylamine, 1.89 g (0.01 mole) of SarBoc and 1.15 g (0.01 mole) of N-hydroxysuccinimide are dissolved in 100 ml of chloroform, 2.06 g of dicyclohexylcarbodiimide are then added, with agitation, and the agitation is maintained for 24 hours. The precipitate of dicyclohexylurea is then removed, the solvent is evaporated off from the filtrate and the residue is taken up in 100 ml of acetone in order to remove the remaining solid dicyclohexylurea. The desired product precipitates when a volume of water is added to the filtrate. After the precipitate has been washed with an acetone/water mixture, x$_g$ of C12SarBoc are obtained.

Preparation of C12Sar hydrochloride: The product obtained above is dissolved in 80 ml of THF; 20 ml of a 5N solution of hydrochloric acid in diethyl ether are added and the mixture is left to stand for 24 hours at ambient temperature, during which time the final hydrochloride precipitates. It is isolated by filtration at 0° C., washed with ice THF and dried in vacuo. This gives C12Sar.HCl.

isolation of C12Sar$_1$: The salt obtained above is dissolved in 50 ml of methanol; 100 ml of a 0.1N aqueous solution of sodium hydroxide are added and the solvents are evaporated off in vacuo at ambient temperature to a volume of about 25 ml. This solution is poured into 100 ml of water and the aqueous phase is extracted with 100 ml and then 50 ml of ethyl acetate. The organic phases are combined and dried over sodium sulfate. The solvent is then removed in vacuo at 0° C.

The residue is purified by chromatography on a column of silica gel using, as the eluent, a solution of methanol containing 1% by volume of aqueous ammonia solution (about 30%).

This gives 2.05 g of C12Sar$_1$ having a melting point of 39° C.

(e) Synthesis of C12Sar$_2$ and C12Sar$_3$

The same process as that described for the synthesis of C12Sar$_1$ is applied, but C12Sar$_1$ and C12Sar$_2$, respectively, are used as the starting materials.

The yields are comparable.

C12Sar$_2$: melting point 58° C.

C12Sar$_3$: melting point 66°–67° C.

(f) Synthesis of C16Sar$_{1,2,3}$

Figure 2:
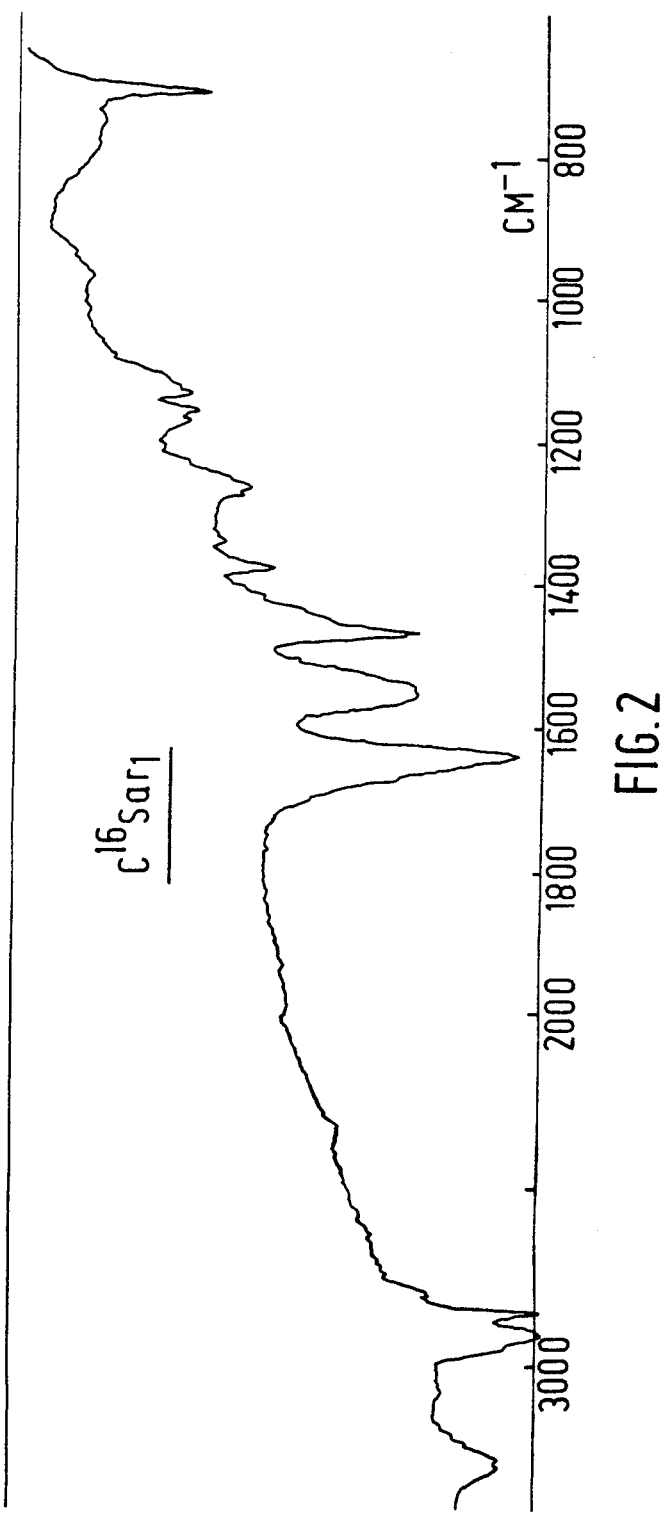
Figure 3:
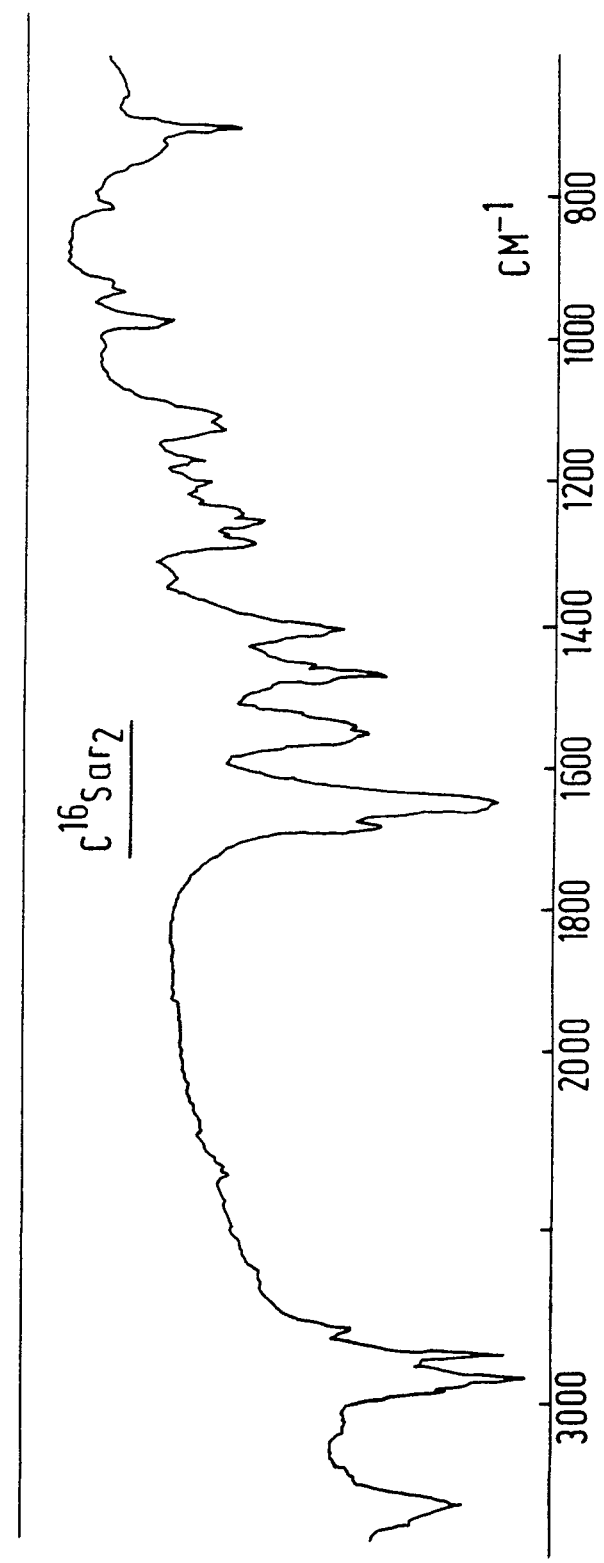
Figure 4:
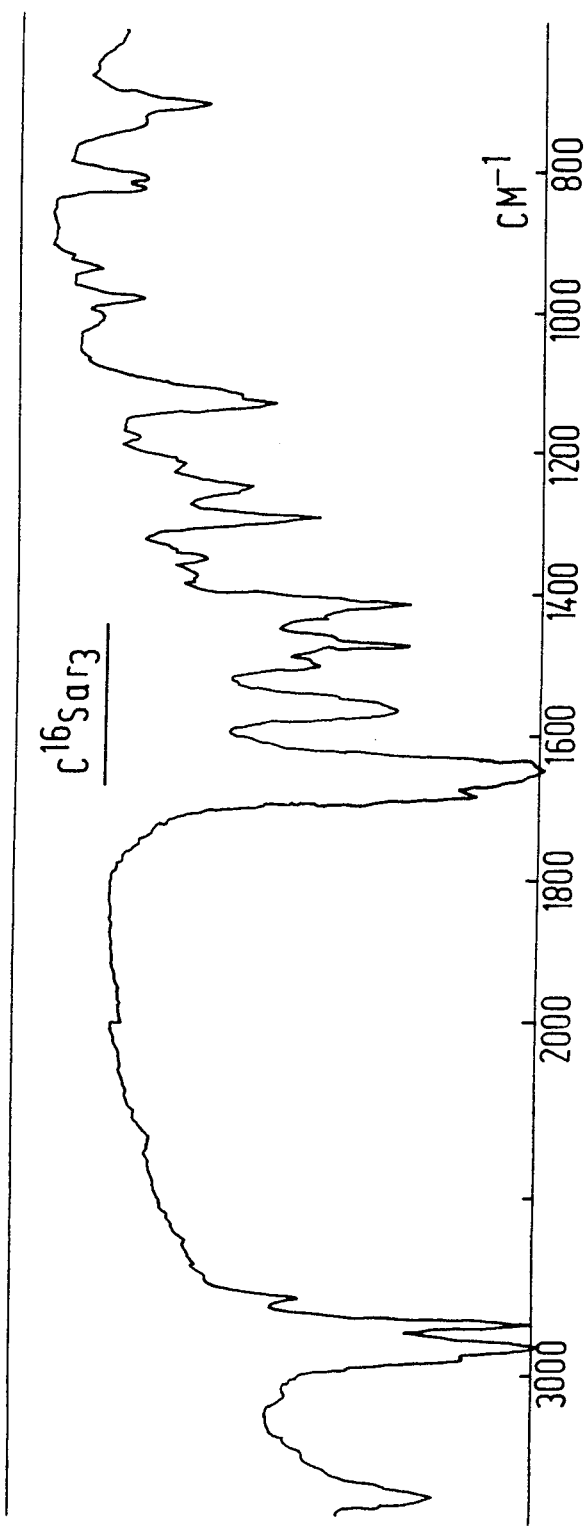

The procedures described under (d) and (e) are applied in order to prepare these derivatives, the infrared spectra of which (in KBr) are shown respectively in FIGS. 2, 3 and 4.

(g) Synthesis of C18Sar$_2$ 2.3 g (0.02 mole) of sarcosine NCA are added in small portions to a solution of 2.69 g (0.01 mole) of octadecylamine in 150 ml of chloroform, with vigorous agitation. The solvent is then removed, the residue is dissolved in diethyl ether and the latter is then removed in vacuo at a temperature of the order of 0° C.

This gives 4 g of a product whose average degree of polymerization, measured by determining the terminal amine group with perchloric acid in acetic acid, is very close to 2.

By chromatography on a column of silica gel using, as the eluent, methanol containing 1% of concentrated aqueous ammonia solution, C18Sar$_1$, C18Sar$_2$, C18Sar$_3$ and C18Sar$_4$ are separated to give more than 60% of C18Sar$_2$. There is also a small amount of C18Sar$_5$ and a trace of C18Sar$_6$ with a residue of starting amine.

The C18Sar$_2$ thus obtained, even when not separated from its homologs, has emulsifying properties comparable to those of the C18Sar$_2$ obtained by the SarBoc method.

The structure of lipopeptides according to the invention was studied by the technique of X-ray diffraction.

It was thus possible to establish that the amphiphatic lipopeptides have mesophases of periodic structure in aqueous solution for water concentrations of less than about 60%, and that the periodic structure can be preserved in the dry state by slow evaporation of the water from the mesophase. The amphiphatic lipopeptides according to the invention thus constitute a new class of lyotropic liquid crystals and they can have the same applications as these liquid crystals.

The structure of the amphiphatic lipopeptides is now described in greater detail with reference to the example of the lipopeptides C17Sar$_p$, consisting of an aliphatic chain possessing 17 carbon atoms and of a polysarcosine chain, the degree of polymerization of which was varied from 1 to 60.

The lipopeptides C17Sar$_p$ exhibit a dual polymorphism: on the one hand as a function of the length of the polypeptide chain and on the other hand as a function of their water content. According to their composition, the lipopeptides adopt three types of structure: lamellar for degrees of polymerization (DP) of less than 9, hexagonal for DP values of between 10 and about 35, and centered cubic for DP values of more than about 35. Furthermore the lipopeptides can exhibit a polymorphism as a function of the water content of their mesophases. The addition of water modifies the ratio of the volumes of the hydrophilic and hydrophobic sequences and can cause the structure to change from lamellar to hexagonal (for DP values of between 5 and about 9) or from hexagonal to cubic (for DP values of between 17 and about 35).

The invention therefore also relates to the application of the amphiphatic lipopeptides to the composition of lyotropic liquid crystals.

The mesophases of amphiphatic lipopeptides can also incorporate numerous components, both hydrophilic and hydrophobic, such as: alcohols, acids, paraffins, carnation oil, ethyl stearate, isopropyl palmitate and the like, and can thus give, for example, milks or creams, the viscosity of which can easily be varied by altering the structure of the mesophases, this structure itself being determined by the respective length of the hydrophobic and peptide sequences in the lipopeptides.

The emulsifying properties of the amphiphatic lipopeptides with respect to numerous pairs of immiscible liquids, such as water/hydrocarbons and water/base products of the cosmetic industry, were also tested. The type and the stability of the emulsions obtained were studied by the method of selective staining, the method of dilution, the electrical conductivity, the breaking properties of freezing, and electron microscopy.

To obtain emulsions, about 1% by weight of amphiphatic lipopeptide ($CnSar_p$ with n=16, 17 or 18 and p=1, 2 or 3, for example) is added to the two immiscible liquids, the mixture is shaken for 10 to 15 minutes and the emulsion forms easily. This method was used to prepare emulsions of different compositions, from 30 to 70% of each component, with the systems water/octane, water/isopropyl myristate, water/isopropyl palmitate, water/butyl or ethyl stearate, water/carnation oil, water/vaseline oil, water/cosbiol and water/mygliol). The emulsions obtained are very stable (several months) and withstand temperature increases up to about 60° C. The viscosity, compactness and unctuousness of the emulsions are modified by varying the lipopeptides content between 1 and 2%.

The invention therefore also relates to the application of the amphiphatic lipopeptides as emulsifiers and to the emulsion incorporating amphiphatic lipopeptides as emulsifying agents, present in an amount by weight of the order of 1% or more.

The solubility of the lipopeptides and their affinity for different solvents can be varied as desired by modifying the number of carbon atoms in the hydrophobic chain and the nature of the peptide chain. It is also possible easily to modify the hydrophilic-hydrophobic balance of such lipopeptides by modifying the number of carbon atoms in the hydrophobic chain and the degree of polymerization of the peptide chain.

The amphiphatic lipopeptides according to the invention readily give very stable emulsions for very low lipopeptide contents (about 1% by weight), whereas it is necessary to have 15–16% of the conventional surface-active agents. Furthermore, they have the advantage of being produced with natural components (lipids and peptides). These amphiphatic lipopeptides can be applied as emulsifying agents for immiscible media in a very wide variety of fields, for example in the cosmetics industry (moisturising creams, antiwrinkle creams, varnishes, solvents for varnishes, and the like), in the food industry (mustards, mayonnaises and the like) and in the petroleum industry (additives for oils, assisted recovery of petroleum), inter alia.

TABLE I
Nomenclature of the peptide sequences

| Designation | Name of the polypeptide | Formula of the side chain |
|---|---|---|
| Eb | Poly(benzyl glutamate) | $-(CH_2)_2-COO-CH_2-C_6H_5$ |
| Ep | Poly(hydroxypropyl-glutamine) | $-(CH_2)_2-CO-NH-(CH_2)_3OH$ |
| Ee | Poly(hydroxyethyl-glutamine) | $-(CH_2)_2-CO-NH-(CH_2)_2OH$ |
| E | Poly(glutamic acid) | $-(CH_2)_2-COOH$ |
| Db | Poly(benzyl aspartate) | $-CH_2-COO-CH_2-C_6H_5$ |
| D | Poly(aspartic acid) | $-CH_2-COOH$ |
| Kt | Poly(trifluoroacetyl-lysine) | $-(CH_2)_4-NH-CO-CF_3$ |
| K | Polylysine | $-(CH_2)_4-NH_2$ |
| S | Polyserine | $-CH_2-OH$ |
| T | Polythreonine | $-CH-OH$ <br> $\|$ <br> $CH_3$ |
| Sar | Polysarcosine (+) | |

(+) Polysarcosine:

$$(-N-CH_2-CO-)_n$$
$$\;\;|$$
$$CH_3$$

We claim:

1. An amphiphatic lipopeptide of the formula $CnSar_p$ wherein
Cn is a hydrophobic aliphatic amine having n carbon atoms,
n is a whole number from 8 to 24, inclusive,
Sar is a unit which has the structure of sarcosine linked through a peptide linkage to Cn or to another Sar, and
p defines the degree of polymerization and is a positive whole number of at least one.

2. An emulsion of immiscible media, which contains at least about 1% of a lipopeptide as claimed in claim 1.

3. A lipopeptide as claimed in claim 1 having a lamellar structure.

4. A lipopeptide as claimed in claim 1 having a hexagonal structure.

5. A lipopeptide as claimed in claim 1 having a centered cubic structure.

6. The lipopeptide as claimed in claim 1 which is $C17Sar_{20}$.

7. An amphiphatic lipopeptide $CnSar_p$ according to claim 26, wherein n is 16, 17 or 18 and p is 1, 2 or 3.

8. A lipopeptide as claimed in claim 7 which is $C16Sar_{1-3}$.

9. A lipopeptide as claimed in claim 7 which is $C17Sar_{1-3}$.

10. A lipopeptide as claimed in claim 7 which is $C18Sar_1$.

11. A lipopeptide as claimed in claim 7 which is $C18Sar_2$.

12. A lipopeptide as claimed in claim 7 which is $C18Sar_3$.

13. A process of preparing a lyotropic liquid crystal which comprises dissolving in water a lipopeptide as claimed in claim 1 in an amount of at least about 60 percent and, optionally, evaporating water slowly from the resulting solution.

14. In emulification of immiscible liquids with an emulsifying agent, the improvement wherein the emulsifying agent is a lipopeptide as claimed in claim 1.

15. A liquid crystal the essential components of which are at least one lipopeptide as claimed in claim 1 and water.

* * * * *